United States Patent [19]

Dorf et al.

[11] 4,399,357
[45] Aug. 16, 1983

[54] METHOD AND APPARATUS FOR INSPECTING GLASS CONTAINERS

[75] Inventors: Arthur L. Dorf; Sam Lovalenti, both of Toledo, Ohio

[73] Assignee: Owens-Illinois, Inc., Toledo, Ohio

[21] Appl. No.: 266,576

[22] Filed: May 22, 1981

[51] Int. Cl.³ .............................. B67C 1/14; B07C 5/00
[52] U.S. Cl. .................................. 250/223 B; 209/526; 356/240
[58] Field of Search ............................ 250/227, 223 B; 356/239, 240, 428; 209/526

[56] References Cited

U.S. PATENT DOCUMENTS

| | | | |
|---|---|---|---|
| 3,328,000 | 6/1967 | Rottmann | 250/223 |
| 3,394,263 | 7/1968 | Baker | 250/223 |
| 3,894,806 | 7/1975 | Remy et al. | 356/240 |
| 4,063,823 | 12/1977 | Grat | 356/197 |
| 4,066,363 | 1/1978 | Juvinall | 356/198 |
| 4,209,802 | 6/1980 | Fogg et al. | 358/106 |

*Primary Examiner*—David C. Nelms
*Assistant Examiner*—J. Jon Brophy
*Attorney, Agent, or Firm*—Gerald T. Welch; Myron E. Click; David H. Wilson

[57] ABSTRACT

This invention relates to inspecting glass containers and other types of containers for defects, such as horizontal checks, in the sidewall thereof. The invention involves both method and apparatus for inspecting for such defects, whereby radiant energy is directed from above to be transmitted through the sidewall as a vertical band or column while the container is rotated. A light-sensitive detector observes the sidewall for reflected light produced by the defect, energizing of the detector creating a reject signal for rejection of flawed containers.

7 Claims, 2 Drawing Figures

METHOD AND APPARATUS FOR INSPECTING GLASS CONTAINERS

This invention relates to inspecting glass containers and other types of containers having transparent or translucent sidewalls for defects, and especially to inspecting glass containers for defects such as horizontal checks in the sidewall thereof.

BACKGROUND OF THE INVENTION

In the manufacture of glass containers, a defect that is sometimes found which is difficult to detect comprises a generally horizontal check or mirror-like flaw in the wall of the container. It is essential that such defects or flaws be detected even though they be few in number, with respect to the total number of containers being manufactured.

The prior art has employed various types of inspection devices primarily relying on illuminating the defect and then reading the presence of reflected light emitted by the defect. The following U.S. patents all relate to such devices which are satisfactory to a greater or lesser degree in detecting such defects. The patents are:

U.S. Pat. No. 3,328,000: Rottmann
U.S. Pat. No. 3,349,906: Calhoun et al
U.S. Pat. No. 3,415,370: Husome
U.S. Pat. No. 3,529,167: Calhoun
U.S. Pat. No. 3,601,616: Katsumata
U.S. Pat. No. 3,651,937: Kronseder
U.S. Pat. No. 3,834,429: Schulz
U.S. Pat. No. 3,987,301: O'Conner
U.S. Pat. No. 4,002,823: Van Osterhout
U.S. Pat. No. 4,140,901: Fischer et al
U.S. Pat. No. 4,171,481: Mima et al
U.S. Pat. No. 4,213,042: Beach et al
U.S. Pat. No. 4,221,961: Peyton All of the aforesaid patents involve methods and apparatus different from, and generally more complex methods and apparatus than the present invention.

SUMMARY OF THE INVENTION

It is an object of the present invention to provide method and apparatus for quickly inspecting hollow containers for horizontal checks in the walls thereof and rejecting those containers having such defects or flaws.

It is a further object of the present invention to provide such method and apparatus wherein the containers can be inspected immediately after forming and annealing while they are relatively cool or cold, following such operations.

Another object of the invention is to provide such method and apparatus which is relatively simple and economical whereby the containers can be inspected with rotation in a very expedient manner.

Generally, the invention comprises moving the hollow containers successively through an inspection station, momentarily interrupting the lateral movement of each container and axially rotating same at the inspection station, directing a concentrated source of radiant energy to which the container is transparent downwardly through a localized region of the finish portion to thereby illuminate the sidewall therebelow, and causing a portion of the light to be redirected by any existent checks. The redirected light is sensed by a light sensitive detector such as a video camera stationarily mounted facing and adjacent to the container sidewall. The redirected sensed light is detected by the sensor during axial rotation of the container at the inspection station and the sensor produces a reject signal for rejection of the flawed container.

DESCRIPTION OF THE PREFERRED EMBODIMENT

Figure 1:
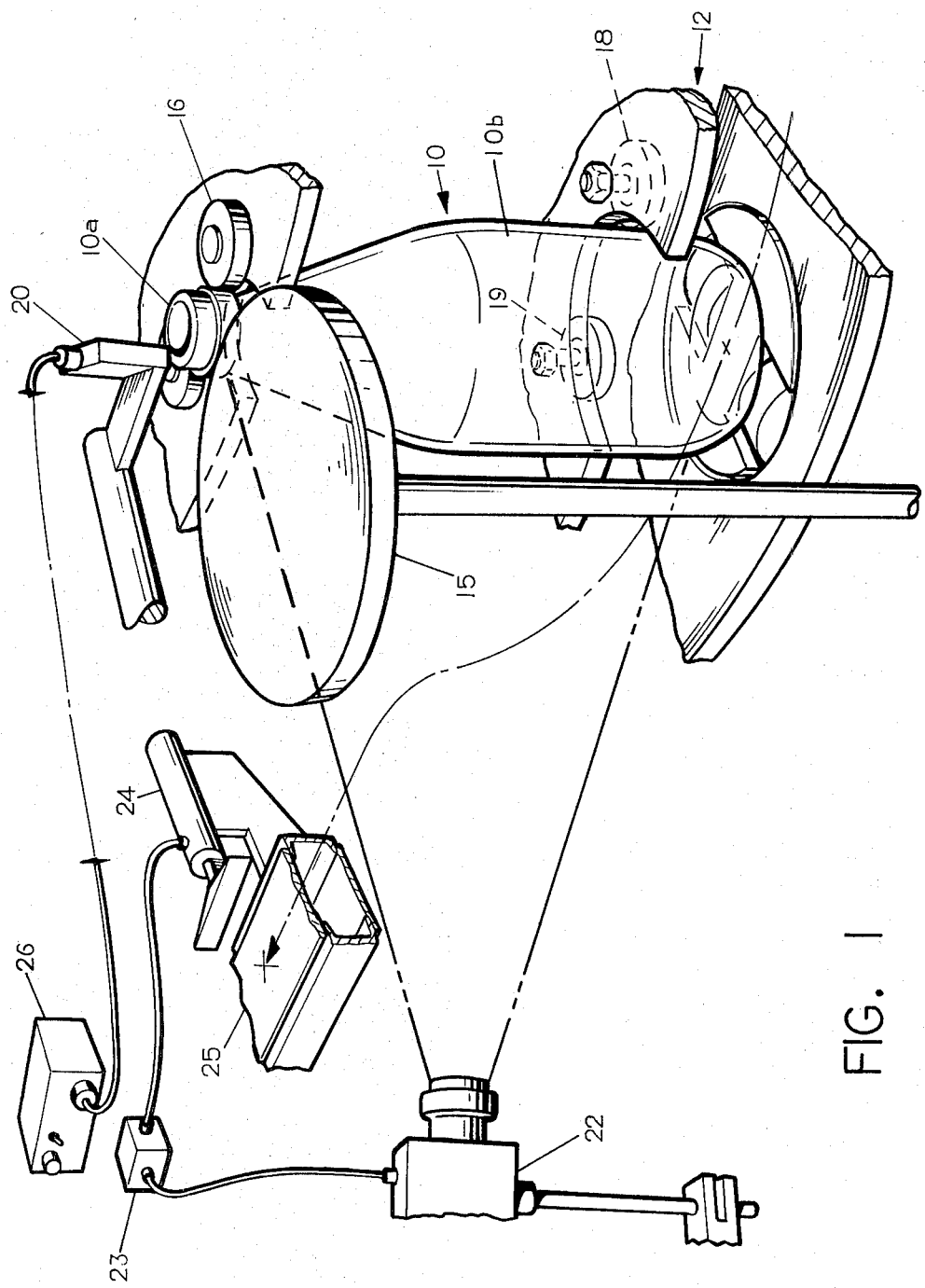
FIG. 1 is a diagrammatic perspective view of an apparatus embodying the present invention.

Referring to the drawings, the containers 10 are adapted to be moved through an inspection station on a rotary inspection machine, such as by a starwheel mechanism, as is known in the art. The rotary inspection machine (not shown), and specifically its starwheel mechanism 12, moves each container 10 in upright position to the inspection station, where its lateral movement is interrupted momentarily by stopping the starwheel for the required inspection interval. Normally, the containers are newly-formed but not sufficiently hot to require special handling techniques or non-checking materials to handle the same. The inspection is preferably conducted immediately following the annealing procedure to remove inherent stresses from the containers while they are at ambient temperature.

When each container 10 is positioned at the inspection station, it is rotated axially by a large powered roller 15 which contacts the finish portion of the container. The container finish is backed thereat by a pair of freely-rotatable smaller rollers 16 and 17, which retain the opposite side of the finish. Another pair of freely-rotatable smaller rollers 18 and 19 is located at a lower region beneath rollers 16 and 17, respectively, to support the lower region of the container during rotation. At such time, the container is preferably resting on a non-rotatable disc or pad on a horizontal level immediately below the starwheel 12.

With the container in proper position for inspection, a source of radiant energy such as provided by an incandescent light contained in a box 26 is directed through a bundle of glass fibers in the form of a light pipe 20 is directed downwardly through a localized portion of the container finish 10a. The light pipe 20 is aimed directly downwardly onto the container lip so that the light is transmitted through the finish 10a and downwardly through the sidewall 10b of the container. Such container is transparent to such transmitted light, the finish and sidewall serving as a further conduit for the light. The light pipe 20 is mounted closely adjacent and facing the finish in stationary relation to direct a narrow vertical band of light downwardly through the container finish and sidewall. The width of the light pipe 20 is generally complemental to the container wall thickness at the finish area.

Figure 2:
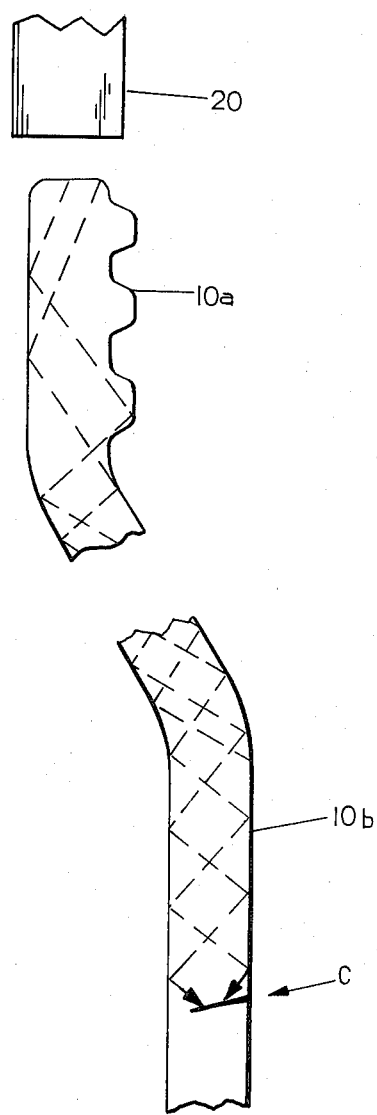
FIG. 2 is an enlarged vertical sectional view of the finish and defect-bearing sidewall of the glass container being inspected, illustrating the manner in which the finish receives the light and the check reflects the light.

The downwardly-directed light follows the interior of the sidewall and is interiorly reflected therewithin and constitutes an extension of the light pipe. Such interior lighting is shown diagrammatically in FIG. 2 of the drawings by the broken line arrows.

If a defect or flaw, such as a horizontal check C is present in the sidewall of the container 10, a portion of the internally-transmitted light is redirected exteriorly into a light sensor 22 such as a video camera. The sensor which is sensitive to the radiant energy emitted by the light pipe 20 is mounted alongside the container facing the entire container sidewall which is in its viewing area.

The sensor 22 in the form of video camera is preferably arranged to scan a vertical band of the container sidewall which is illuminated by the light pipe 20, being in vertical alignment therewith. Thus, during axial rotation of the container, all of its sidewall areas are illuminated and simultaneously scanned by the light sensitive device or sensor 22. If a defect such as a check C is present, the redirected portion of the light is caused to pass through the container surface exteriorly and horizontally to be detected by the sensor.

The sensor 22 comprising a video camera is preferably a linear array camera. Such video camera is a linear array of discrete light-sensitive diodes which view the container, such as a bottle, in a vertical direction. The diodes are sequentially electronically interrogated (scanned) to determine which diodes have seen an increase in light intensity which results in a greater output voltage from these diodes. One can then compare voltages from adjacent diodes or ratios of voltages to detect a bright signal and measure the intensity and location of the signal. Also, since the container is rotating while the array is being scanned, each scan sees a different vertical segment of the container. Therefore, by keeping track of how many scans a signal is present, at about the same vertical height on the container, the length of the check can be determined. This can be used to differentiate between checks and other inhomogenities which may be present but are not a cause for rejection, such as small seeds. The scan information is used to produce a reject signal. The reject signal serves to energize a reject mechanism 24 mounted at a subsequent point along an off-loading conveyor 25 onto which the starwheel 12 discharges the inspected containers.

Thus, the present invention provides an improved method and apparatus for inspecting the sidewalls of hollow transparent containers for horizontal checks or interior flaws. Such defects can be efficiently and expediously determined in glass containers whether they be formed of clear flint glass or colored glass. While the containers must be rotated about a central axis, such movement requires only one 360° revolution and can be achieved in a small fraction of a second for each container. Defects, whether they be relatively small or large, so long as they exhibit an appreciable horizontal component, can be detected by the present invention. The light pipe 20 serves to deliver a vertical band or column of relatively-bright light into the sidewall portion under observation, thus permitting ready detection of horizontally-transmitted reflected light of sufficient intensity for ready observation.

The present invention provides a method and apparatus for detecting horizontal checks in the sidewall of transparent containers, wherever they may be located, by illuminating the finish from above. The primary purpose is to enhance the horizontal checks in the transparent container to allow their detection and subsequent rejection of the container by a side-wall inspection gauge or device dedicated to check detection. This invention illuminates horizontal checks or vertical checks having a horizontal component and makes their detection possible.

The present invention lends itself to application to existing inspection machines performing multiple inspecting functions at a series of sequential inspection stations mounted on a circular machine, for example. The apparatus of this invention may be mounted at one of such stations for horizontal check detection.

Various modifications and other embodiments of the present invention may be restored to within the spirit and scope of the appended claims.

We claim:

1. The method of inspecting glass containers and the like for horizontal checks in the sidewall thereof wherein the containers are moved successively in upright position to and through an inspection station, and are rotated about their vertical axes thereat, comprising directing a source of light to which the said container is transparent, downwardly onto the top surface of the finish of said container at a limited position thereof during its rotation to illuminate a vertical section of the wall, viewing the illuminated vertical section of the wall with a vertical, linear, diode array and electronically scanning the diode array while the container is rotated through at least 360° of rotation whereby a complete scan of the sidewall is made.

2. The method in accordance with claim 1, wherein the said light source is positioned at one end of a glass fiber bundle and the other end of said bundle is directed vertically downwardly at a localized area of the finish portion of said container.

3. An apparatus for inspecting glass containers and the like for horizontal checks in the wall thereof which comprises means for moving upright containers successively into and through an inspection station, means at said inspection station for rotating said container about its vertical axis at said inspection station, means at said inspection station for directing a source of radiant energy to which the said container is transparent downwardly into the top surface of finish portion of said container at a specific radial position during its rotation, thereby illuminating a vertical section of the container wall, light sensitive means mounted at said inspection station and facing the illuminated portion of said container wall, said light sensitive means being a vertical, linear diode array, and means connected to said array for creating a signal in response to the energization of a diode in said light sensitive device.

4. The combined apparatus set forth in claim 3, wherein said means for directing a source of radiant energy at said container comprises an electrical light source and a glass fiber bundle in alignment with said source, said bundle being directed vertically downwardly at said radial position of the finish portion of said container.

5. The combined apparatus set forth in claim 4, wherein the said glass fiber bundle has a width comparable to the wall thickness of said finish portion at said radial position.

6. The combined apparatus set forth in claim 3, wherein the said light-sensitive device further comprises a video camera with means for vertically scanning successively, the diode array whereby the sidewall of said container is inspected during its rotation.

7. The combined apparatus set forth in claim 3, further including means responsive to said signal for rejecting a defective container.

* * * * *